United States Patent [19]

Högnelid et al.

[11] Patent Number: 5,632,267

[45] Date of Patent: May 27, 1997

[54] HEART DEFIBRILLATOR AND DEFIBRILLATION METHOD WHEREIN DEFIBRILLATION IS ACHIEVED BY HIGH-FREQUENCY, LOW-ENERGY PULSES

[75] Inventors: Kurt Högnelid, Bromma; Kjell Noren, Solna, both of Sweden

[73] Assignee: Pacesetter AB, Solna, Sweden

[21] Appl. No.: 521,039

[22] Filed: Aug. 29, 1995

[30] Foreign Application Priority Data

Aug. 29, 1994 [SE] Sweden ................. 9402865

[51] Int. Cl.$^6$ .......................... A61N 1/39
[52] U.S. Cl. ............................... 607/5
[58] Field of Search ...................... 607/4, 5, 7

[56] References Cited

U.S. PATENT DOCUMENTS

| | | | |
|---|---|---|---|
| 4,088,140 | 5/1978 | Roekland et al. | 607/14 |
| 4,735,206 | 4/1988 | Hewson . | |
| 5,107,834 | 4/1992 | Ideker et al. . | |
| 5,174,289 | 12/1992 | Cohen | 607/9 |
| 5,265,600 | 11/1993 | Adams et al. | 607/4 |
| 5,282,837 | 2/1994 | Adams et al. | 607/5 |
| 5,488,198 | 1/1996 | Ayers et al. | 607/4 |

FOREIGN PATENT DOCUMENTS

| | | |
|---|---|---|
| 0420563 | 4/1991 | European Pat. Off. . |
| 0588125 | 3/1994 | European Pat. Off. . |
| 0588127 | 3/1994 | European Pat. Off. . |

OTHER PUBLICATIONS

"Current Problems in Cardiology®- Implantable Cardioverters and Defibrillators," Troup, vol. XIV, No. 12, Dec., 1989, pp. 729–731.

*Primary Examiner*—William E. Kamm
*Attorney, Agent, or Firm*—Hill, Steadman & Simpson

[57] ABSTRACT

An implantable heart defibrillator contains a pulse generator controlled by a control unit for emitting a number of heart stimulation pulses at a rate of several Hertz or more. The control unit causes the pulse generator to emit heart stimulation pulses with an energy content of the same, or somewhat greater, magnitude than conventional pacemaker pulses for a period of time long enough for the entire heart to become refractory.

43 Claims, 3 Drawing Sheets

HEART DEFIBRILLATOR AND DEFIBRILLATION METHOD WHEREIN DEFIBRILLATION IS ACHIEVED BY HIGH-FREQUENCY, LOW-ENERGY PULSES

BACKGROUND OF THE INVENTION

1. Field of the Invention

The present invention relates to an implantable heart defibrillator and to a defibrillation method.

2. Description of the Prior Art

It is known that cardiac fibrillation can be triggered by a low-voltage alternating current applied between the tip of an ordinary, implanted pacemaker electrode and an indifferent electrode in the body, e.g. the pacemaker enclosure. Thus, atrial fibrillation can be triggered by an alternating current, with a peak-to-peak amplitude of 18 V, applied via a 2 kohm series resistance to an electrode in the atrium. A lower series resistance could trigger ventricular fibrillation. Ventricular fibrillation can otherwise be induced by an alternating current with an amplitude of e.g. 18 volts peak-to-peak, applied, via a 0.5 kohm series resistance, to an electrode in the ventricle. For fibrillation to be induced, the alternating current must be applied for a number of time periods lasting 1 to 2 s with inter-period intervals of the same duration.

Once fibrillation has been triggered, it can, as is known, be terminated with a defibrillator supplying a brief, powerful discharge pulse with a voltage on the order of 1,000 V and an energy content of 4 to 40 J. When defibrillation is successful, i.e. fibrillation is terminated, the heart can then immediately resume normal rhythm, indicating that an optimum energy level was selected for the defibrillation pulse, e.g. 40 J applied externally. If cardiac arrest occurs, this indicates that more energy, e.g. 120 J applied externally, was used than was needed for restoration of normal heart rhythm. In the latter instance, additional defibrillation must be considered, however, the heart can often be induced to resume normal rhythm if subjected to conventional pacemaker stimulation at e.g. 70/min. In order to achieve the most rapid possible recovery of the heart, this stimulation should be terminated as soon as sinus rhythm is detected. Recovery is then very rapid, and the heart usually returns to its normal state after about 10 minutes.

The above-described mechanism for triggering heart fibrillation with the aid of a low-voltage alternating current can also be used for terminating fibrillation. One example thereof is the external AC defibrillators employed during the defibrillator's infancy. These employed an alternating current with several hundred volts and a frequency of 50–60 Hz. See Paul J. Troop, "Implantable Cardioverters and Defibrillators", Current Problems in Cardiology, Volume XIV, No. 12, Dec. 1989, pp. 729–731.

European Application 0 588 127 describes an implantable heart defibrillator which utilizes the heart's anisotropic properties for making cells, having a certain "preferred" orientation, refractory by means of preparatory, relatively low-energy pulses. Fibrillation can then be stopped with a subsequent defibrillation shock with less energy than would be required in conventional defibrillation. Defibrillation can sometimes be achieved solely with the preparatory, low-energy pulses without any subsequent defibrillation pulse. These preparatory, low-energy pulses are emitted for a period of time lasting from 10 ms up to the duration of a refractory period.

European Application 0 588 125 discloses heart defibrillation using defibrillation sequences consisting of low-energy stimulation pulses, and conventional defibrillation shocks. The low-energy stimulation pulses cause defibrillation of parts of the heart, mainly those regions around the electrode used, whereas conventional defibrillation shocks are required to defibrillate the rest of the heart. The amplitude and duration of the low-energy stimulation pulses used significantly exceed pacemaker pulses.

SUMMARY OF THE INVENTION

An object of the present invention is to provide an implantable defibrillator which makes defibrillation possible using much less energy than is possible in known defibrillators.

The above object is achieved in accordance with the principles of the present invention in a method and an implantable apparatus for defibrillating a heart, wherein a number of cardiac stimulation pulses are emitted at a rate of several Hertz or more, and wherein stimulation pulses are emitted with an energy content of the same, or somewhat larger, magnitude than conventional pacemaker pulses for a period time which is long,enough for the entire heart to become refractory.

In defibrillation according to the invention, the heart is thus converted from a state of fibrillation, in which more or less chaotic conditions prevail in the different parts of the heart, to a known state, resembling cardiac arrest, from which the heart can spontaneously resume its normal state or be stimulated into assuming its normal state. Since the heart stimulation pulses used have an energy content of the same, or somewhat larger, magnitude than those emitted by ordinary pacemakers, total energy consumption for defibrillation of a heart is considerably less than has hitherto been required.

According to one embodiment of the defibrillator of the invention, the control unit causes the pulse generator to emit stimulation pulses for a period of one or several seconds so that the entire heart becomes refractory.

According to another embodiment of the defibrillator of the invention, the control unit reduces the pulse generator's pulse rate to a normal pacing rate after the aforementioned period of time. This ensures that the heart reverts to its normal state after defibrillation it may be appropriate for the normal heart rate to be achieved after a period lasting several seconds. This reduction in rate can advantageously be performed according to an appropriate, continuous curve.

In another embodiment of the defibrillator of the invention, the pulse generator can be arranged to emit monophasic or biphasic pulses. The monophasic pulses can consist of half-periods of sinusoidal voltage, and the biphasic pulses can consist of whole-period sinusoidal voltage, thereby simplifying the design of the pulse generator. The period of the sinusoidal oscillation must be brief, compared to the duration of the refractory period.

According to another embodiment of the defibrillator of the invention, a detector is arranged to locally detect when heart cells exit the refractory state, and the control device causes the pulse generator to emit a stimulation pulse immediately thereafter. The detector can advantageously be arranged to locally detect the end of the T-wave. Each stimulation pulse then captures a small area around the electrode or electrodes, and the area becomes refractory. Cells closest to the electrodes will then be the first ones to exit the refractory state. A new stimulation then follows, whereupon all the old area plus a number of non-refractory cells outside this area are captured and made refractory. This procedure is repeated, more and more cells then being captured and made refractory, so that the entire heart, or a large part thereof, becomes refractory after a sufficient number of stimulation pulses. In this embodiment, the stimulation interval has essentially the same duration as the refractory period, i.e. about 150 ms.

The detector can advantageously be connected to a bipolar electrode with a small distance between the poles. This makes local detection possible without any significant noise interference from the surroundings.

According to another embodiment of the defibrillator of the invention, the pulse generator emits stimulation pulses to the heart across an electrode for pacemaker stimulation. Alternatively, a number of variously sited electrode systems can be arranged for transmitting stimulation pulses, with an electrode switching unit being provided to connect the different electrode systems to the pulse generator for pulse emission according to a define pattern. In this way, the distribution of current can be varied throughout the heart, so the heart is made refractory more effectively, and more efficient defibrillation of the heart is achieved.

According to another embodiment of the defibrillator of the invention, the pulse generator first emits a low-energy defibrillation or cardioversion pulse with several joules of energy before emission of heart stimulation pulses, at a rate of several Hertz or more, starts. Thus, treatment commences with a small shock-cardioversion, to ensure that a sufficiently large refractory "starting" area is created around the electrode, before treatment continues with the heart stimulation pulses emitted at a rate of several Hertz or more.

DETAILED DESCRIPTION OF THE PREFERRED EMBODIMENTS

Figure 1:
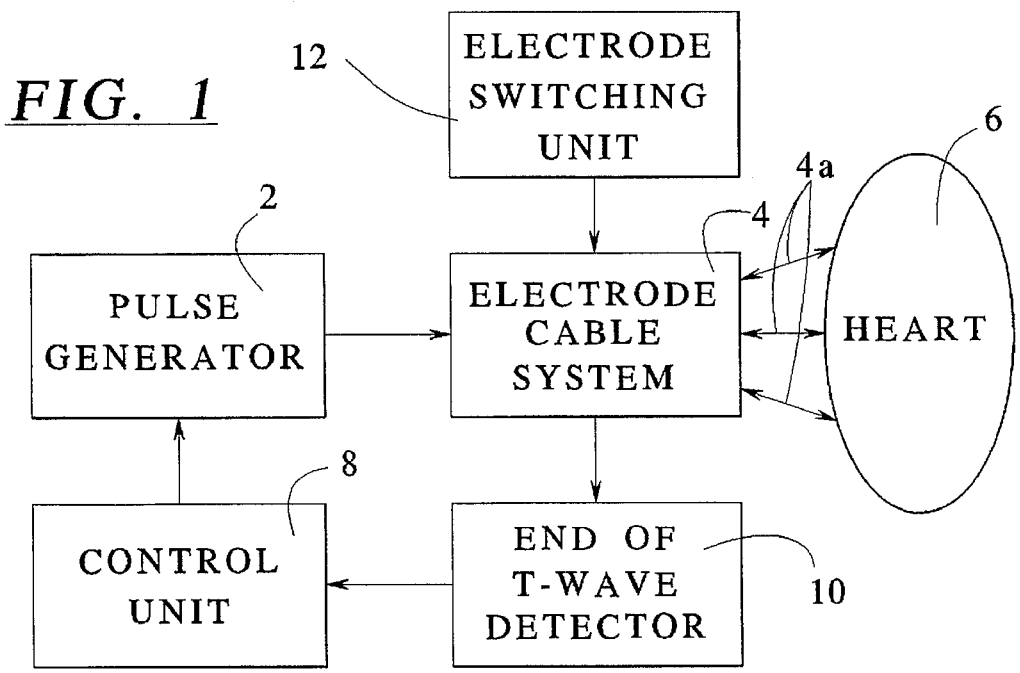
FIG. 1 is a block diagram of one embodiment of a defibrillator according to the invention.

In the embodiment shown in FIG. 1, a pulse generator 2, via an electrode cable system 4 having one or more electrode leads 4a (cables) respectively carrying one or more electrodes, is connected to a heart 6 for supplying stimulation pulses thereto. The pulse generator 2 is controlled by a control unit 8. A detector 10 is arranged to sense heart activity via the electrode cable system 4, and to send detected information to the control unit 8 for controlling the pulse generator 2 in accordance therewith. An electrode switching unit 12 is devised to connect different combinations of the electrodes of the leads 4a of the electrode cable system 4 to the pulse generator 2 according to a defined pattern or in some optional way.

The defibrillator shown in FIG. 1 can be operated in the following manner.

Figure 8:
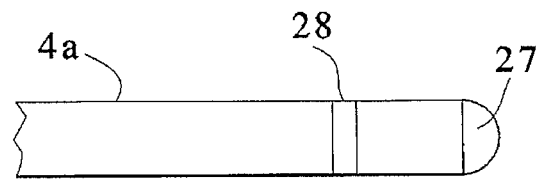
FIG. 8 shows the distal end of one embodiment of a lead suitable for use in the defibrillator according to the invention.

Stimulation pulses are emitted by the pulse generator 2 each time heart cells locally exit their refractory state. The detector 10 detects when heart cells locally leave the refractory state in a fibrillating heart 6 such as by detecting the end of the T-wave, whereupon this information is sent to the control unit 8 which causes the pulse generator 2 to immediately emit a new stimulation pulse. For this detection, the detector 10 is connected to a bipolar electrode as shown in FIG. 8, with the electrode poles very close to each other, in the heart 6. This therefore makes possible local measurement of conditions between the electrode poles with minimum noise interference from the surroundings. The electrode can, e.g., have a tip-ring configuration with the ring 28 arranged at a very small distance from the tip 27.

After a stimulation pulse, the cells closest to the electrodes exit their refractory state first, whereupon a new stimulation pulse is emitted which accordingly converts all the "old" area of the heart, plus a number of additional non-refractory cells outside this area, to the refractory state. This procedure is repeated so that increasing numbers of heart cells are captured in a "synchronized" area. This converts the entire heart to the refractory state after a sufficient number of stimulation pulses.

The duration of the refractory state is 150 to 250 ms. The stimulation rate is therefore on the order of 5 Hz.

After the entire heart has become refractory, the stimulation rate can be slowly reduced, allowing the heart to resume a normal operating rhythm in the normal way. Alternatively, the heart can be stimulated at a normal pacemaker rate of, typically, 70/min. In order to achieve the fastest possible recovery of the heart, stimulation in the latter instance should be terminated as soon as sinus rhythm is detected.

It may be advantageous to have a number of differently sited electrodes as schematically represented by the differently sited arrows 4a shown in FIG. 1, connected in an optional manner or according to a defined pattern with the electrode switching unit 12, in the heart. If this approach is adopted, an electrode should be located in the vicinity of the bundle of His, since depolarization waves propagated on normal signal pathways from the A-V node move more rapidly than other waves.

It is also possible to first create a refractory "starting" area in the heart by emitting a low-energy defibrillation pulse or cardioversion pulse of several joules and then to switch to the above-described defibrillation method.

The defibrillator according to the invention can clearly be used without this ability to switch between variously sited electrode systems, and a conventional pacemaker electrode, appropriately placed in the ventricle, can advantageously be used. The invention can also be employed, however, for terminating atrial fibrillation.

One alternative way of operating the defibrillator according to the invention is to start with a fast stimulation rate, much faster than the fibrillation rate, which normally amounts to about 300/min, i.e. the corresponding period is about as long as the refractory period of the heart cells.

Figure 6:
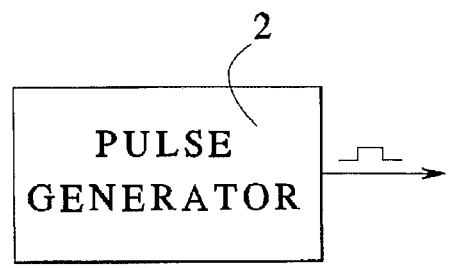
FIGS. 6 and 7 respectively show different pulse waveforms which can be emitted by the pulse generator of the defibrillator according to the invention.
Figure 7:
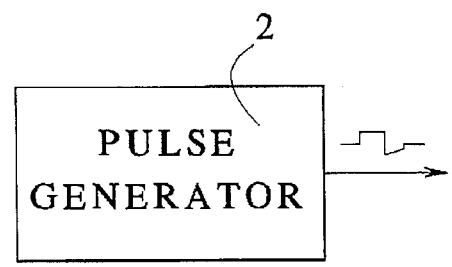

The defibrillator can therefore be operated so as to first emit a series of stimulation pulses at a fast rate, e.g. 50 Hz. The pulses can be monophasic (FIG. 6) or biphasic (FIG. 7), and the amplitude can be, e.g., 20 V. The pulses can consist of a half period (monophasic) or a whole period (biphasic) with a 50 Hz alternating current. This sequence of high-frequency stimulation pulses can be sent by the pulse generator 2 to the heart over a defined period of time. The goal is to make the entire heart refractory.

After this high-frequency period, there is a change to a normal stimulation phase, achieved by a rapid reduction in the rate at which pulses are emitted by the pulse generator 2. The amplitude of the pulses can simultaneously be reduced to a normal pacemaker level of about 5 V. Controlling the pulse generator 2 in such a way that this normal level is reached several seconds after the high-frequency phase starts may be appropriate.

The pulse generator can be controlled so the rate for the pulses varies according to a semi-Gaussian curve, i.e.

$$f = f_0 \cdot k_1 \cdot e^{-k_2 \cdot t^2}$$

whereby f designates the frequency, $f_0$ designates the starting rate, e.g. 50 Hz, $k_1$ and $k_2$ designate constants and t designates the time.

Figure 2:
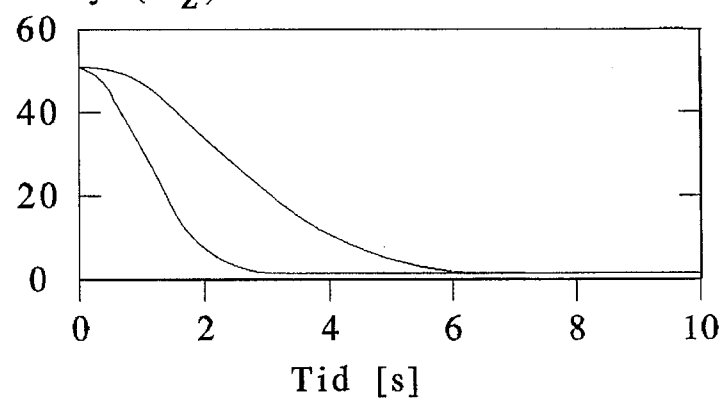
FIGS. 2 and 3 show examples of continuous frequency control for the emission of stimulation pulses by the defibrillator according to the invention.

One such frequency variation over time is shown in FIG. 2.

Figure 3:
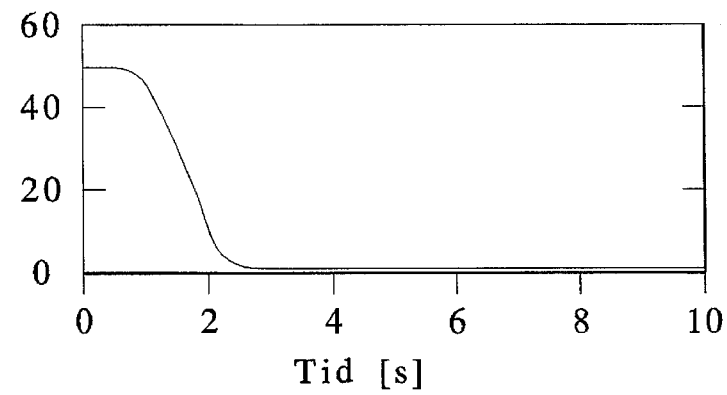

Alternatively, frequency control can be according to a higher order exponential equation, i.e.

$$f = f_0 \cdot k_1 \cdot e^{-k_2 \cdot t^4}$$

as illustrated in FIG. 3, if a faster drop in rate is desired after the high-frequency phase.

Figure 4:
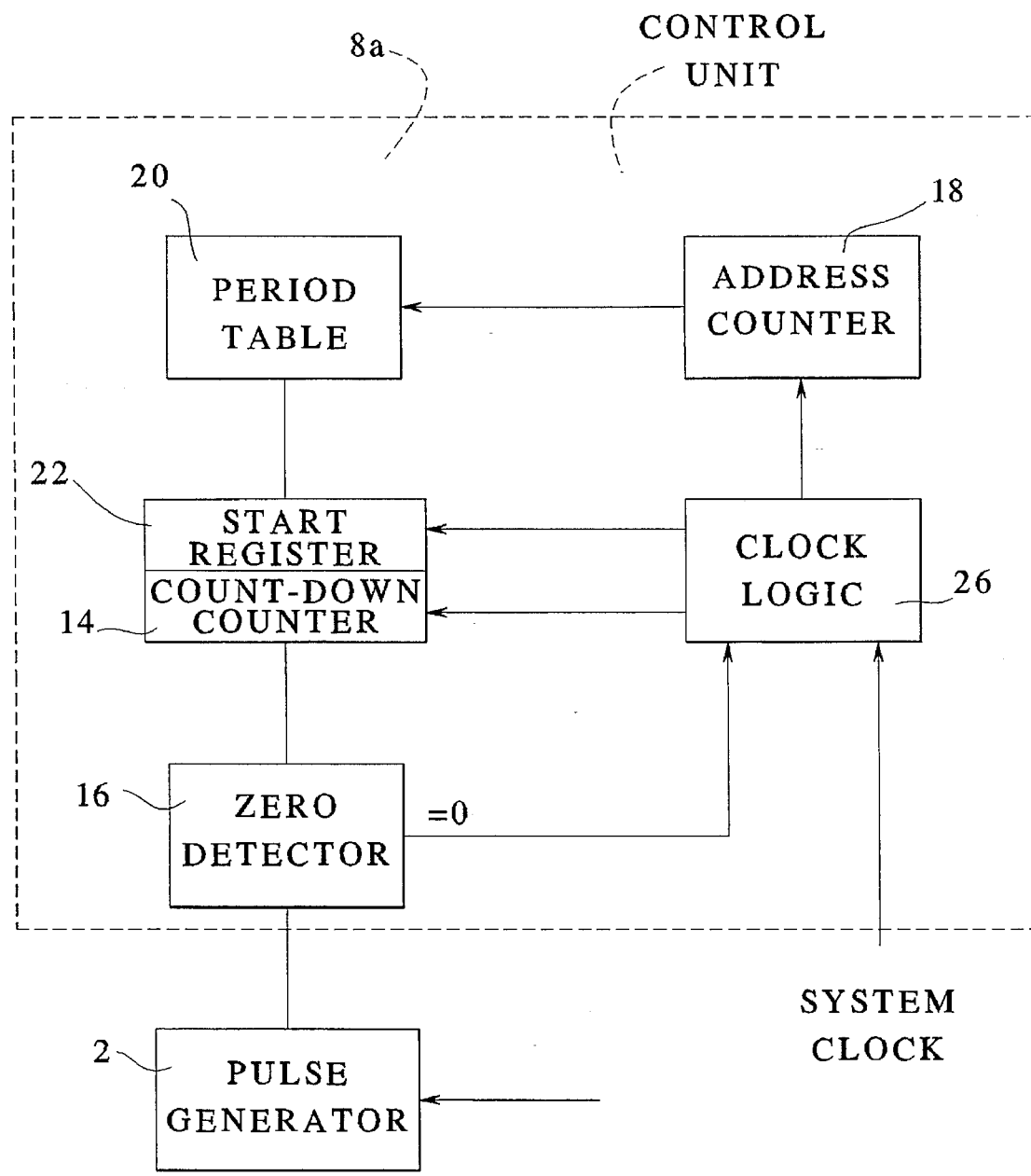
FIG. 4 is an exemplary block diagram of one embodiment for achieving such frequency control.
Figure 5:
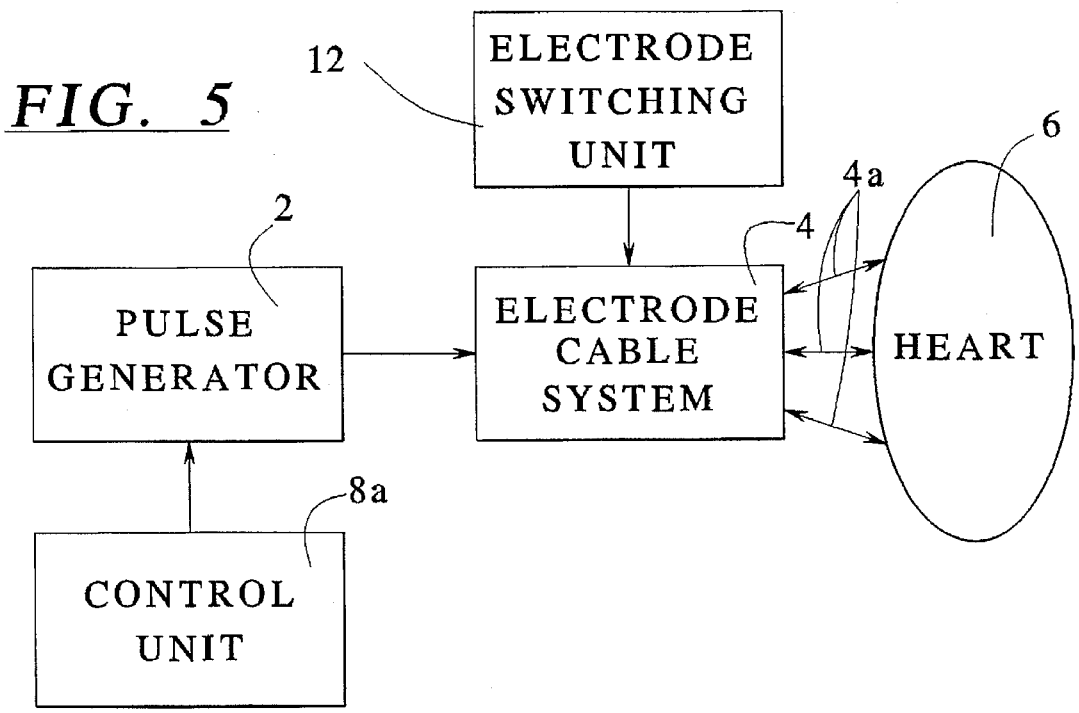
FIG. 5 is a block diagram of another embodiment of defibrillator according to the invention.

FIG. 4 shows how frequency control of the kind illustrated in FIGS. 2 and 3 can be achieved. In this version of the derfibrillator according to the invention, the frequency control arrangement shown in FIG. 4 is contained in a control unit 8a shown in the block diagram of FIG. 5. Since no detection of the refractory period takes place in this embodiment, there is no need for the detector 10 shown in FIG. 1.

When the count-down timer 14 passes zero, which is detected with the zero detector 16, the address counter 18 increases one step, and the next period duration is downloaded from the period table 20 to the start register 22 of the counter 14. At the same time, a triggering pulse is sent to the pulse generator 2 for emission of a stimulation pulse to the heart through the electrode cable 4. A new count-down phase then starts. When the count-down timer 14 again reaches zero, the process is repeated with downloading of the next period duration, etc.

The arrangement shown in FIG. 4 also contains a clock for controlling the count-down counter 14 and the requisite clock logic 26.

The pulse generator 2 is naturally also devised so the amplitude of output pulses can be controlled.

Although modifications and changes may be suggested by those skilled in the art, it is the intention of the inventors to embody within the patent warranted hereon all changes and modifications as reasonably and properly come within the scope of their contribution to the art.

We claim as our invention:

1. A heart defibrillator comprising:

a pulse generator which emits electrical pulses each having an amplitude less than or equal to about 5 V;

electrode means adapted for delivering said electrical pulses in vivo to a defibrillating heart;

means for identifying a period of time for making said heart entirely refractory by delivery of said electrical pulses thereto; and control means for controlling said pulse generator for causing said pulse generator to emit said electrical pulses at a rate faster than or equal to about 5 Hertz for said period of time.

2. A defibrillator as claimed in claim 1 wherein said control means comprises means for causing said pulse generator to emit said pulses at a rate of approximately 10 Hertz.

3. A defibrillator as claimed in claim 1 wherein said means for identifying a period of time for making said heart entirely refractory comprises means for setting said period equal to at least one second and wherein said control means comprises means for causing said pulse generator to emit said pulses for said period of time of at least one second.

4. A defibrillator as claimed in claim 1 wherein said control means comprises means for causing said pulse generator to emit monophasic pulses as said electrical pulses.

5. A defibrillator as claimed in claim 4 wherein said control means comprises means for causing said pulse generator to emit monophasic pulses each comprising a half-period of a high-frequency sinusoidal voltage.

6. A defibrillator as claimed in claim 1 wherein said control means comprises means for causing said pulse generator to emit biphasic pulses as said electrical pulses.

7. A defibrillator as claimed in claim 6 wherein said control means comprises means for causing said pulse generator to emit a biphasic pulse complex consisting of one period of a high-frequency sinusoidal voltage.

8. A defibrillator as claimed in claim 1 wherein said heart, when entirely refractory, consists of cells in a refractory state, and wherein said means for identifying a period of time for making said heart entirely refractory comprising detector means for locally detecting when cells of said heart exit said refractory state, and said control means comprises means for causing said pulse generator to emit a stimulation pulse immediately after said cells exit said refractory state.

9. A defibrillator as claimed in claim 8 wherein said detector means comprises means for locally detecting an end of a T-wave from said heart.

10. A defibrillator as claimed in claim 8 wherein said detector means includes a bipolar electrode having a distal end and two poles at said distal end with a small distance between said poles.

11. A defibrillator as claimed in claim 1 wherein said electrode means comprises a pacemaker lead having a distal end with a tip electrode disposed at said distal end.

12. A defibrillator as claimed in claim 1 wherein said electrode means comprises a plurality of electrodes adapted to be differently cited with respect to said heart, and wherein said defibrillator further comprises electrode switching means for electrically connecting different electrodes to said pulse generator for delivering said electrical pulses in a defined pattern.

13. A defibrillator as claimed in claim 1 wherein said control means comprises means for controlling said pulse generator to initially emit a low-energy defibrillation/cardioversion pulse having an energy content of several joules before emission of said electrical pulses at the rate of approximately one Hertz.

14. A defibrillator comprising:

a pulse generator which emits electrical pulses each having an amplitude in a range from about 5 V to about 20 V;

electrode means adapted for delivering said electrical pulses in vivo to a fibrillating heart;

means for identifying a period of time for making said heart entirely refractory by delivery of said electrical pulses thereto; and control means for continuously reducing the rate of emission of said pulses from said pulse generator from a starting rate which is faster than 300 pulses per minute during said period of time for making said heart entirely refractory.

15. A defibrillator as claimed in claim 14 wherein said control means comprises means for continuously reducing the rate of emission of said pulses from said pulse generator according to a predetermined function.

16. A defibrillator as claimed in claim 15 wherein said control means comprises means for reducing said emission rate of said pulse generator according to a predetermined function selected from the group consisting of Gaussian functions and exponential curve functions having an order of two or higher.

17. A defibrillator as claimed in claim 14 wherein said means for identifying a period of time for making said heart entirely refractory comprises means for setting said period equal to at least one second and wherein said control means comprises means for causing said pulse generator to emit said electrical pulses at a rate of approximately 10 Hertz for said period of time of at least one second.

18. A defibrillator as claimed in claim 14 wherein said control means comprises means for causing said pulse generator to emit monophasic pulses as said electrical pulses.

19. A defibrillator as claimed in claim 18 wherein said control means comprises means for causing said pulse generator to emit monophasic pulses each comprising a half-period of a high-frequency sinusoidal voltage.

20. A defibrillator as claimed in claim 14 wherein said control means comprises means for causing said pulse generator to emit biphasic pulses as said electrical pulses.

21. A defibrillator as claimed in claim 20 wherein said control means comprises means for causing said pulse generator to emit a biphasic pulse complex consisting of one period of a high-frequency sinusoidal voltage.

22. A defibrillator as claimed in claim 14 wherein said electrode means comprises a pacemaker lead having a distal end with a tip electrode disposed at said distal end.

23. A defibrillator as claimed in claim 14 wherein said electrode means comprises a plurality of electrodes adapted to be differently cited with respect to said heart, and wherein said defibrillator further comprises electrode switching means for electrically connecting different electrodes to said pulse generator for delivering said electrical pulses in a defined pattern.

24. A method for defibrillating a heart comprising the steps of:
   emitting electrical pulses each having an amplitude less than or equal to about 5 V from a pulse generator;
   delivering said electrical pulses in vivo to a fibrillating heart;
   identifying a period of time for making said heart entirely refractory by delivery of said electrical pulses thereto; and
   controlling said pulse generator for causing said pulse generator to emit said electrical pulses at a rate of several Hertz for said period of time.

25. A method as claimed in claim 24 wherein the step of controlling said pulse generator comprises causing said pulse generator to emit said pulses at a rate of approximately 10 Hertz.

26. A method as claimed in claim 24 wherein the step of identifying a period of time for making said heart entirely refractory comprises setting said period of time equal to at least one second, and wherein the step of controlling said pulse generator comprises causing said pulse generator to emit said pulses for said period of time of at least one second.

27. A method as claimed in claim 24 wherein the step of controlling said pulse generator comprises causing said pulse generator to emit monophasic pulses as said electrical pulses.

28. A method as claimed in claim 27 wherein the step of controlling said pulse generator comprises causing said pulse generator to emit monophasic pulses each comprising a half-period of a high-frequency sinusoidal voltage.

29. A method as claimed in claim 24 wherein the step of controlling said pulse generator comprises causing said pulse generator to emit biphasic pulses as said electrical pulses.

30. A method as claimed in claim 29 wherein the step of controlling said pulse generator comprises causing said pulse generator to emit a biphasic pulse complex consisting of one period of a high-frequency sinusoidal voltage.

31. A method as claimed in claim 24 wherein said heart, when entirely refractory, consists of cells in a refractory state, and the step of identifying a period of time for making said heart entirely refractory comprises locally detecting when cells of said heart exit said refractory state, and wherein the step of controlling said pulse generator comprises causing said pulse generator to emit a stimulation pulse immediately after said cells exit said refractory state.

32. A method as claimed in claim 31 wherein the step of detecting when said cells of said heart exit said refractory state comprises locally detecting an end of a T-wave from said heart.

33. A method as claimed in claim 24 further comprising differently siting a plurality of electrodes with respect to said heart, and electrically connecting different electrodes to said pulse generator by switching for delivering said electrical pulses in a defined pattern.

34. A method as claimed in claim 24 wherein the step of controlling said pulse generator comprises controlling said pulse generator to initially emit a low-energy defibrillation/ cardioversion pulse having an energy content of several joules before emission of said electrical pulses.

35. A method for fibrillating a head comprising the steps of:
   emitting electrical pulses each having an amplitude in a range from about 5 V to about 20 V from a pulse generator;
   delivering said electrical pulses in vivo to a fibrillating heart;
   identifying a period of time for making said head entirely refractory by delivery of said electrical pulses thereto; and
   controlling said pulse generator by continuously reducing a rate of emission of said pulses from said pulse generator from a starting rate which is faster than 300 pulses per minute during said period of time for making said heart entirely refractory.

36. A method as claimed in claim 35 wherein the step of controlling said pulse generator comprises continuously reducing the rate of emission of said pulses from said pulse generator according to a predetermined function.

37. A method as claimed in claim 36 wherein the step of controlling said pulse generator comprises reducing the rate of emission of said pulses from said pulse generator according to a predetermined function selected from the group consisting of Gaussian functions and exponential curve functions having an order of two or higher.

38. A method as claimed in claim 35 wherein the step of identifying a period of time for making said heart entirely refractory comprises setting said period equal to at least one second and wherein the step of controlling said pulse generator comprises causing said pulse generator to emit said electrical pulses at a rate of approximately 10 Hertz for said period of time of at least one second.

39. A method as claimed in claim 35 wherein the step of controlling said pulse generator comprises causing said pulse generator to emit monophasic pulses as said electrical pulses.

40. A method as claimed in claim 39 wherein the step of controlling said pulse generator comprises causing said pulse generator to emit monophasic pulses each comprising a half-period of a high-frequency sinusoidal voltage.

41. A method as claimed in claim 35 wherein the step of controlling said pulse generator comprises causing said pulse generator to emit biphasic pulses as said electrical pulses.

42. A method as claimed in claim 41 wherein the step of controlling said pulse generator comprises causing said pulse generator to emit a biphasic pulse complex consisting of one period of a high-frequency sinusoidal voltage.

43. A method as claimed in claim 35 further comprising differently siting a plurality of electrodes with respect to said heart, and electrically connecting different electrodes to said pulse generator by switching for delivering said electrical pulses in a defined pattern.

* * * * *